US006957102B2

(12) United States Patent
Silver et al.

(10) Patent No.: US 6,957,102 B2
(45) Date of Patent: Oct. 18, 2005

(54) ENHANCED INTERFACE FOR A MEDICAL DEVICE AND A TERMINAL

(75) Inventors: H. Ward Silver, Vashon, WA (US); D. Craig Edwards, Fall City, WA (US)

(73) Assignee: Medtronic Emergency Response Systems, Inc., Redmond, WA (US)

( * ) Notice: Subject to any disclaimer, the term of this patent is extended or adjusted under 35 U.S.C. 154(b) by 383 days.

(21) Appl. No.: 10/016,507

(22) Filed: Dec. 10, 2001

(65) Prior Publication Data

US 2003/0109904 A1 Jun. 12, 2003

(51) Int. Cl.$^7$ .............................. A61N 1/00; A61B 5/00
(52) U.S. Cl. ........................ 607/2; 128/920; 600/300; 607/60
(58) Field of Search .............................. 607/2, 4–5, 32, 607/60; 600/523, 524, 481, 508; 128/903–904, 920

(56) References Cited

U.S. PATENT DOCUMENTS

| 5,800,473 | A | | 9/1998 | Faisandier ................... 607/59 |
|---|---|---|---|---|
| 6,074,345 | A | * | 6/2000 | van Oostrom et al. ....... 600/300 |
| 6,283,761 | B1 | * | 9/2001 | Joao ........................... 434/236 |
| 6,442,432 | B2 | * | 8/2002 | Lee ............................. 607/59 |
| 6,687,546 | B2 | * | 2/2004 | Lebel et al. .................. 607/60 |
| 2001/0022615 | A1 | * | 9/2001 | Fernandez et al. .......... 348/143 |
| 2002/0023654 | A1 | * | 2/2002 | Webb .......................... 128/899 |
| 2002/0055917 | A1 | * | 5/2002 | Muraca ........................ 707/1 |
| 2003/0025602 | A1 | * | 2/2003 | Medema et al. ........... 340/568.1 |

FOREIGN PATENT DOCUMENTS

| WO | WO 98/24212 A1 | 6/1998 | ............ A61B/5/00 |
|---|---|---|---|
| WO | WO 01/03575 A1 | 1/2001 | ............ A61B/5/00 |
| WO | WO 01/34222 A2 | 5/2001 | ............ A61M/1/00 |
| WO | WO 01/45793 A1 | 6/2001 | .......... A61N/1/372 |

OTHER PUBLICATIONS

Jones, K.L. et al., "A Protocol for Automatic Sensor Detection and Identification in a Wireless Biodevice Network," *Eleventh IEEE Symposium on Computer–Based Medical Systems*, pp. 311–316 (Jun. 12, 1998) (XP–002133125).

Hernández, A.I., et al., "Real–Time ECG Transmission Via Internet for Nonclinical Applications," *IEEE Transactions on Information Technology in Biomedicine* 50(3):253–257, Sep. 2001.

Zou, Y., and Z. Guo, "A Palm Pilot Based Pocket ECG Recorder," *Proceedings of the Joint IEEE–EMBS Third International Conference on Information Technology in Biomedicine: ITAABS–IT IS* 2000, IEEE Computer Society Press, Piscataway, New Jersey, pp. 110–112.

* cited by examiner

*Primary Examiner*—Carl Layno
(74) *Attorney, Agent, or Firm*—Shumaker & Sieffert, P.A.

(57) ABSTRACT

A system is described that comprises a medical device on which is installed a version of software and a software agent communicatively coupled to the medical device without regard to the version of software installed on the medical device. An example of the medical device includes a defibrillator. The software agent may reside in a personal digital assistant and can be operated to communicate with the defibrillator to access the data stored in the defibrillator irrespective of the version of software of the defibrillator.

60 Claims, 9 Drawing Sheets

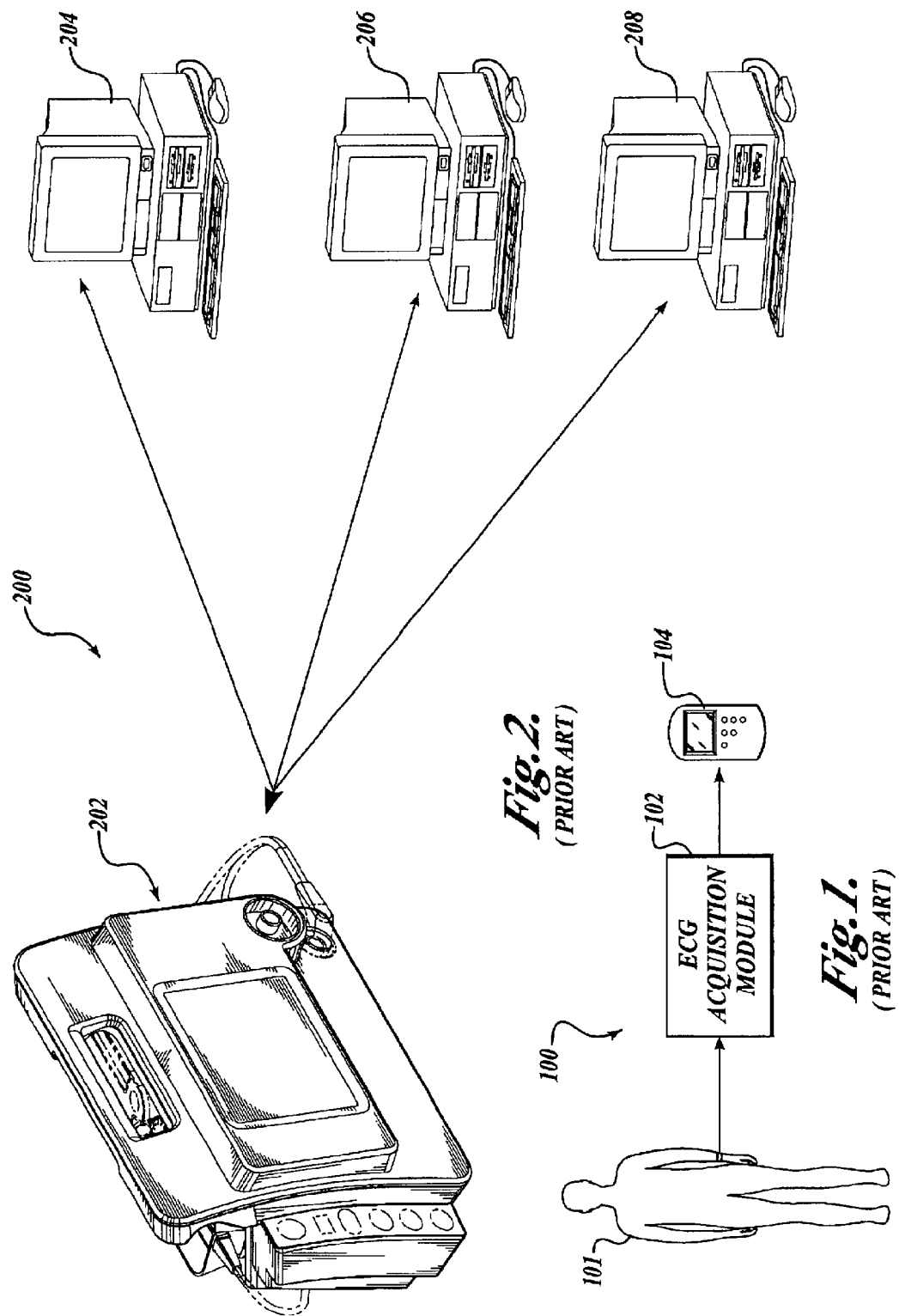

ENHANCED INTERFACE FOR A MEDICAL DEVICE AND A TERMINAL

FIELD OF THE INVENTION

The present invention relates generally to systems for communicating medical information and more particularly, to systems and methods for communicating configuration data and patient data between medical devices and a terminal.

BACKGROUND OF THE INVENTION

In the past, most medical devices operated as stand-alone devices that would either record physiological information from the patient or be operated to supply some therapy or treatment to the patient. FIG. 1 shows a medical system 100 that is limited to monitoring a patient's vital signs and recording physiological information from the patient. The system 100 uses an electrocardiogram acquisition module 102 to acquire electrocardiogram data of a patient 101 and forward such data to a PalmPilot™ 104. The PalmPilot 104 can be controlled to start or stop the recording of the electrocardiogram data. Other information, such as name and age of a patient, can also be recorded along with the electrocardiogram data associated with the patient 101. While recording, the PalmPilot 104 displays the electrocardiogram data as waveforms in real time. The user can change the gain or the zoom to see more details of the waveforms. For proper communications between the electrocardiogram acquisition module 102 and the PalmPilot 104, the PalmPilot 104 must be compatible with the software version installed on the electrocardiogram acquisition module 102.

Other medical devices have advanced to the point where they not only can monitor a patient but they can also apply a therapy to the patient to treat various ailments. These medical devices can be tailored to a particular patient by modifying the parameters relating to a particular medical protocol used to treat the patient. For example, if a patient is in defibrillation, the medical protocol may require a sequence of shocks to be applied to the patient. The energy level of each shock can be modified. Or, the sequencing of a medical protocol can be modified so that the device automatically executes each step in the medical protocol without further human intervention.

To vary or program the parameters of the medical device, the parameters can be retrieved from the medical device. To do that, a terminal is needed to communicate with the medical device because most medical devices do not have a user interface. However, the communication between the terminal and the medical device may be impossible unless the terminal is compatible with the version of software installed on the medical device. The problem is that as different generations of devices and terminals are distributed into the marketplace, it can be exceedingly difficult to obtain a compatible terminal to communicate with the device having a particular version of software. The medical system 100 illustrates such a problem in that if the electrocardiogram acquisition module 102 were to be distributed with a version of software not known to the PalmPilot 104, the PalmPilot 104 may not be able to obtain any physiological information or be able to control the electrocardiogram acquisition module 102.

Furthermore, the current trend among designers of medical equipment is to integrate such equipment into an overall system whereby the equipment can be programmed by an operator in a manner that is specific to a particular patient's needs as well as to have the equipment operate in conjunction with other pieces of the system. In order to facilitate such a system integration, it is necessary to provide a common protocol that can be used to either read data from or write data to a particular medical device. Because many devices have different versions of operating software, it is desirable that communications to these devices operate in a predictable manner regardless of the version of operating software on each device.

Another prior art solution is shown in FIG. 2 where a medical system 200 includes a treatment device 202 that is engineered with all the rules, parameters, and user interface features necessary for the treatment device 202 to communicate with a number of terminals 204–208. In other words, the treatment device 202 contains all of the intelligence necessary to treat a patient as well as the ability to present a user interface to configure the treatment device 202. When one of the terminals 204–208 has successfully connected to the treatment device 202, the treatment device 202 presents a user interface, which is displayed on one of the terminals 204–208, so that a user may control the treatment device 202 or read data from it. To ensure compatibility with multiple generations of terminals 204–208, however, the medical device 202 must be constantly updated and marketed at a price that is prohibitively expensive for many customers.

SUMMARY OF THE INVENTION

To facilitate communication between one or more medical devices and a terminal, the present invention is a communication protocol executed between a medical device and a software agent. The medical device includes a directory of objects that can be accessed by the software agent. Each object includes executing code that can write data to or retrieve data from the medical device irrespective of the version of software installed on the medical device. Each object has a well-known or predefined name so that any software agent may access the well-known name of the object and invoke the executing code of the object.

In one embodiment of the invention, the medical device, such as a defibrillator, can export patient data or configuration data (operating parameters) to the software agent and can have its operating parameters programmed by the software agent.

In one embodiment of the invention, the software agent operates on a computing device, such as a personal digital assistant, which communicates with the medical device through a wired or wireless communication link.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a pictorial diagram illustrating the acquisition of the electrocardiogram data from a patient and the transmission of such data to a PalmPilot™ according to the prior art.

FIG. 2 is a block diagram illustrating communications between a defibrillator and a number of terminals according to the prior art.

DETAILED DESCRIPTION OF THE PREFERRED EMBODIMENT

Figure 3:
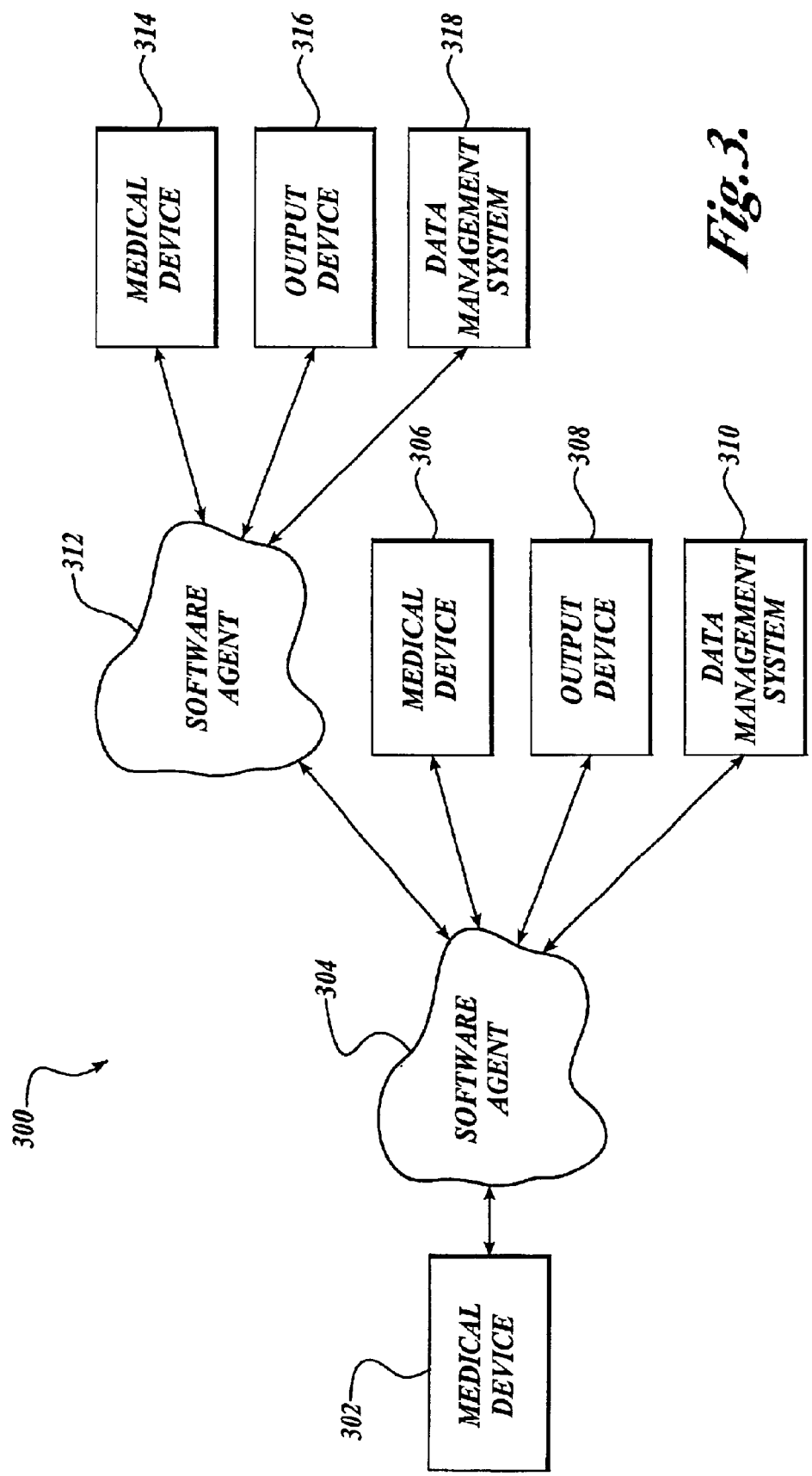
FIG. 3 is a block diagram illustrating communication relationships among a number of medical devices, a number of software agents, a number of output devices, and a number of data management systems according to one embodiment of the invention.

FIG. 3 illustrates one embodiment of a communication system 300 that includes a medical device 302 communicatively coupled to a software agent 304. The medical device 302 is any therapeutic and/or monitoring device, such as a defibrillator, pacer, IV drip pump, etc., that is capable of delivering a therapy to treat a patient or reading patient data such as ECG, blood pressure, etc. The software agent 304 is a software program that can reside in any computer device, such as a personal computer, a personal digital assistant, or other computing device that can execute software instruction to run the software agent 304. The software agent 304 contains instructions to implement a user interface that allows a user to retrieve medical information from the medical device 302 or to configure the medical device 302.

The medical device 302 contains one portion of an interface (described in detail below), and the software agent 304 contains the other portion of the interface. These portions of the interface allow the software agent 304 to communicate to the medical device 302 in a predictable manner regardless of the version of software that is installed on the medical device 302. In this way, communication compatibility between a software agent from one generation and a medical device from another generation is possible. In the example shown in FIG. 3, a software agent 304 communicates with a medical device 302 as well as a medical device 306. With the present invention, communication can take place with both devices even if the medical device 302 is from a different generation than the medical device 306.

One advantage of the ability to communicate with both the medical device 302 and the medical device 306 is best illustrated by an example. Suppose a patient had been successfully treated by the medical device 302 so that the medical device 302 contains medical information regarding the successful treatment that was applied to the patient. At a later point in time, the patient is in need of the same treatment again, but the medical device 302 is at a location that is geographically remote from the patient. The software agent 304 may locate the medical device 302, retrieve the medical information regarding the patient from the medical device 302, such as via a wireless communication link, and configure the medical device 306 so that the medical device 306 may apply the treatment that was successfully applied to the patient by the medical device 302. In this way, medical personnel may reuse a treatment from the medical history of a patient by retrieving medical information from any medical devices that may have treated the patient.

The software agent 304 can also interact with other devices and systems. One example is an output device 308, which includes any devices that can output medical information understandable to a human user, transmit the medical information, or process the medical information. Such output devices 308 can include but are not limited to a printer, a waveform display, a video recorder, a debugging machine, a data card, a cellular phone, a therapeutic device trainer, a modem, an electrocardiogram monitor, a personal computer, an alarm system, a voice storage system, and a personal digital assistant. Another example of a device that can communicate to the software agent 304 is a data management system 310. The data management system 310 is capable of storing, allowing access to, and analyzing the medical information that is obtained by the software agent 304. A further example is a battery that can communicate with the software agent 304 regarding its present capacity so as to alert a user to recharge the battery. An additional example is a service test system or a manufacturing test system that can be controlled by the software agent 304 to calibrate or to obtain a service history of a medical device. As yet another example is another medical device that the software agent 304 may send data for storage.

Besides being capable of interacting with other devices and systems, the software agent 304 can interact with other software agents, such as a software agent 312. The software agent 304 may share with the software agent 312 the medical information obtained from either the medical device 302 or the medical device 306. The software agent 312 may share this medical information with other devices and systems, such as a medical device 314, an output device 316, or a data management system 318.

Each software agent connects a medical device to a diverse group of devices and systems and thereby enhances the functionality of the medical device. Because each software agent can communicate with other software agents, a large network may be formed. The communication medium by which each software agent communicates can be any communication network, such as a wired local area network or a wireless local area network.

Figure 4:
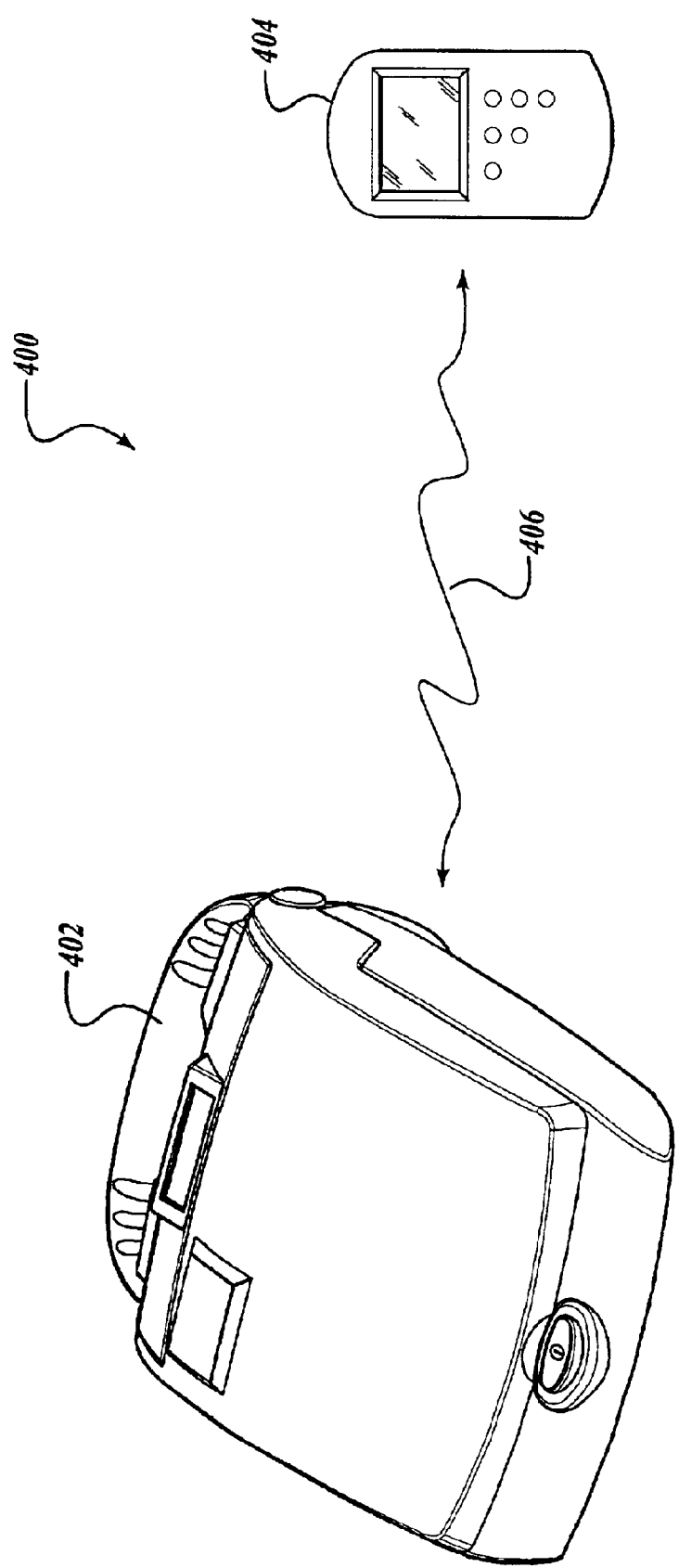
FIG. 4 is a pictorial diagram illustrating a communication relationship between a medical device and a personal digital assistant according to one embodiment of the invention.

In FIG. 4, a system 400 for communicating medical information includes a defibrillator 402, as an example of a medical device, and a personal digital assistant 404, as an example of a terminal or a computing device that can execute the software agent for communicating with the medical device. The defibrillator 402 contains a piece of communication software, and the software agent, which may reside in the personal digital assistant 404 or in another defibrillator (not shown), contains the other piece of the communication software that allows both to communicate through a communication medium 406. The communication medium 406 can be chosen from wired communication protocols or wireless communication protocols.

The defibrillator 402 also includes hardware (not shown) to apply a therapy to a patient according to a set of therapeutic rules. A number of data storage devices (described in further detail below) may be housed in the defibrillator 402 for storing medical information, such as patient data and configuration data. A common interface (also described below) exists in the defibrillator 402 for exporting either the patient data or the configuration data to a device that is external to the defibrillator 402.

The personal digital assistant 404 also includes a number of data storage devices (described below) for storing medical information, such as patient and configuration data obtained from the defibrillator 402, and for storing a set of presentation tools. These presentation tools can be used to invoke a user interface to allow a user to interact with the defibrillator 402. The software agent in the personal digital assistant 404 also provides an interface for importing medical information stored in the defibrillator 402. Via the interface, the software agent allows the user to configure the defibrillator 402 irrespective of the version of software installed on the defibrillator 402.

Figure 5:
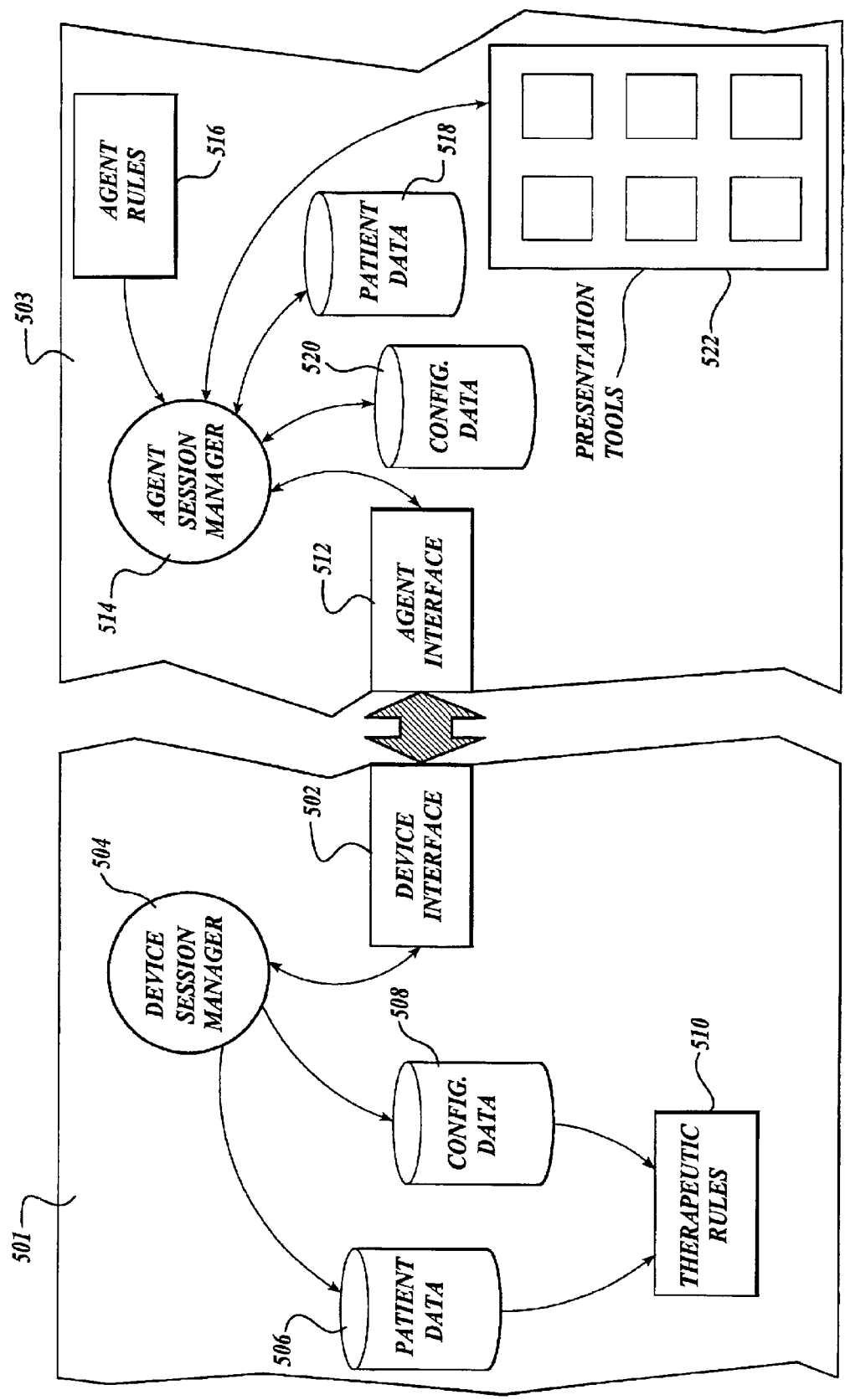
FIG. 5 is a block diagram illustrating internal control/data flow as well as an interface between a medical device and a software agent according to one embodiment of the invention.

FIG. 5 shows these pieces of communications software, as well as other pieces of software in the defibrillator 402, and the software agent, which resides in the personal digital assistant 404. The software 501 running on the defibrillator 402 includes a device interface 502, which exposes certain medical information that can be exported from the defibrillator 402. The term "expose" means making the medical information available in a way that can be accessed by any generation of the software agent. One way to achieve this is to provide a set of application programming interfaces, which provide invocation mechanisms that any software agent may rely on to execute and access the medical information. Another way to achieve this is to provide a number of objects having well-known names (or predefined names) whereby any software agent may use the well-known name of an object to execute the object to retrieve medical information, write medical information, or both.

Examples of medical information include patient data, which is stored in a datastore 506, and configuration data, which is stored in a datastore 508. Both the patient data and configuration data may be modified to affect a therapy that may be applied to a patient by a set of therapeutic rules 510. A device session manager 504 executes the piece of communications software associated with the defibrillator 402 and coordinates the device interface 502, patient data in the datastore 506, and configuration data in the datastore 508.

The software agent running on the personal digital assistant 404 includes an agent session manager 514 for executing the communications software associated with the software agent and coordinating various pieces of software of the software agent. An agent interface 512 allows the software agent to import medical information, which is external to the software agent, such as patient data and configuration data. After the medical information is imported into the software agent, the medical information may be stored in a datastore 518 (if patient data) or in a datastore 520 (if configuration data). One or more presentation tools 522 may be invoked by a set of agent rules 516 when the medical information is imported so that a user interface may be displayed to show the medical information to a user. The user may operate the user interface to query for more information from the defibrillator 402 or to configure the defibrillator 402. The term "configure" includes modifying the configuration and/or patient data, causing any functions of the medical device to be performed, or emulating a front panel that can control the medical device.

The software agent can retrieve medical information in the datastore 506 and the datastore 508 or configure the defibrillator 402 via the device interface 502 and the agent interface 512 irrespective of the version of the software or the medical device or irrespective of the therapeutic rules 510 or the version of the therapeutic rules 510. In this way, any terminal or computing device that executes the software agent, such as the personal digital assistant 404, can communicate with any medical device, such as the defibrillator 402.

Figure 6:
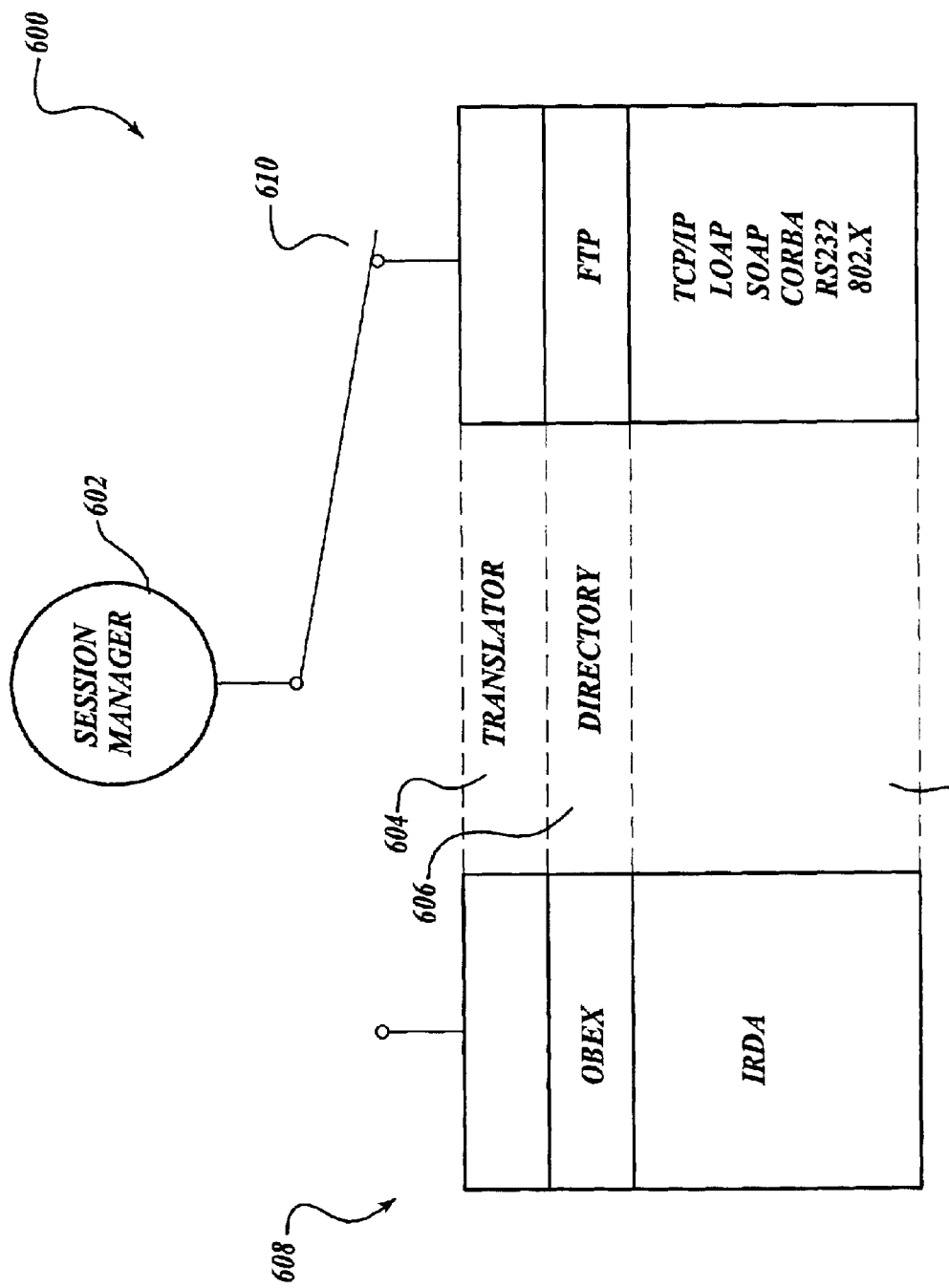
FIG. 6 is a block diagram illustrating two packages of communication software that are selectable by a session manager according to one embodiment of the invention.

A session manager 602 as shown in FIG. 6 represents either the device session manager 504 or the agent session manager 514. The session manager 602 operates in a general manner to get data from a certain location or to put data at a certain location.

At least two types of communication protocols are supported: the wired communication protocols 608 or wireless communication protocols 610. Each set of communication protocols includes a translator layer 604 that hides the implementation of a selected set of communication protocols so as to provide data that is understandable to the session manager 602 without regard to the selected set of communication protocols. Below the translator layer 604 are the communication protocols that make up the two sets of protocols.

A number of communication protocols can be selected. For example, the wireless communication protocols include the Object Exchange (OBEX) protocol, Infrared Data Association (IrDA) protocols, and Bluetooth protocols. The wired communication protocols include File Transfer Protocol (FTP), Transmission Control Protocol (TCP), Internet Protocol (IP), Lightweight Directory Access Protocol (LDAP), Simple Object Access Protocol (SOAP), Common Object Request Broker Architecture (CORBA) protocol, RS-232-C protocol, HyperLAN, and IEEE 802.x protocols. The OBEX protocol or the FTP protocol accesses data that is organized in a directory so that a layer that contains these protocols is also known as a directory layer 606.

Figure 7:
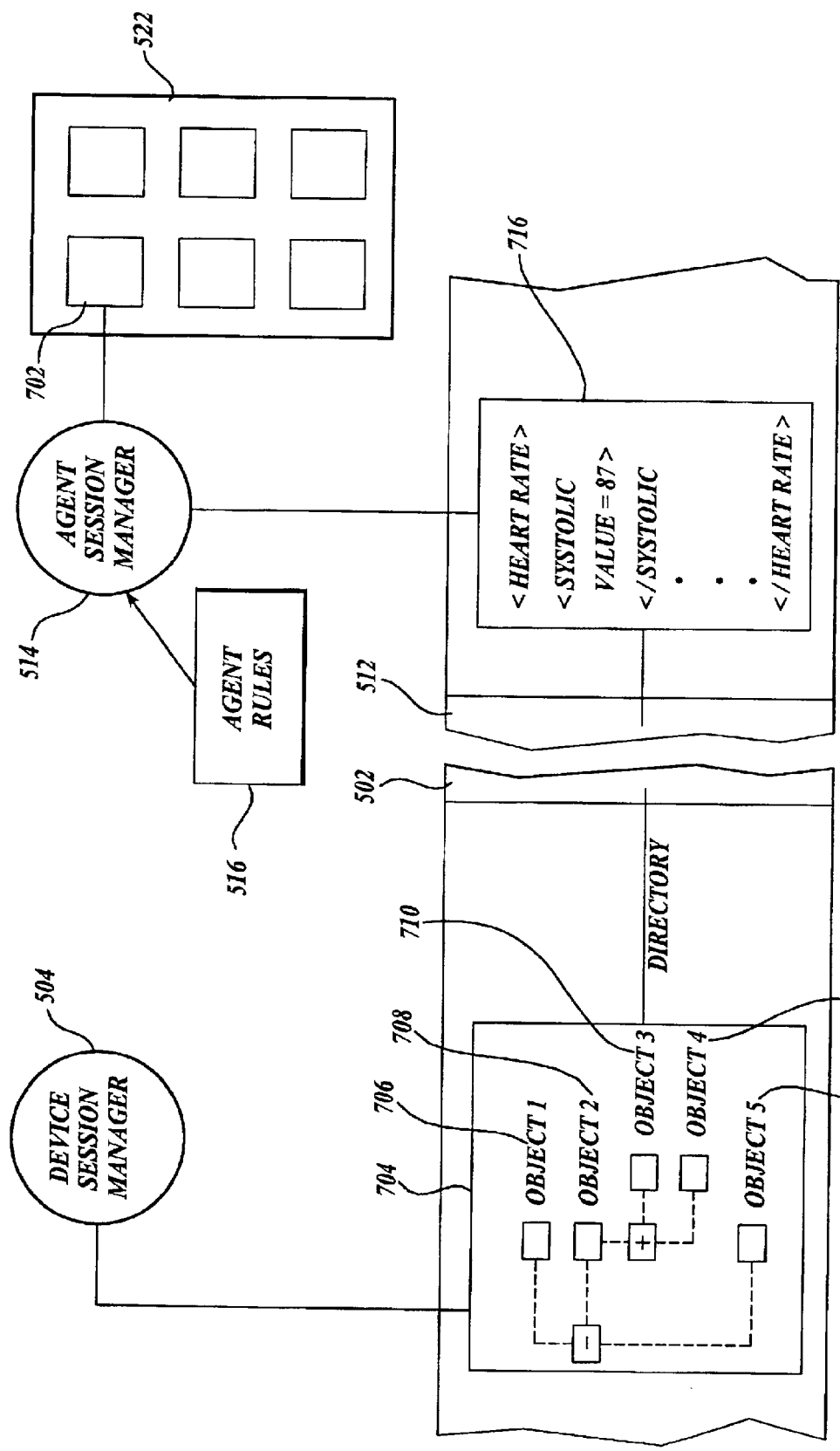
FIG. 7 illustrates in greater detail the interface between a medical device and a software agent according to one embodiment of the invention.

As shown in FIG. 7, medical information on the defibrillator 402, which is accessible by the software agent residing on the personal digital assistant 404, is exposed by the device session manager 504 as a number of objects in a directory 704. Objects 706–714 are organized as an inbox, an outbox, device data, patient data, and a root directory. An object can contain other objects, such as object 708, and in such a case, the object being contained is considered a subdirectory. There can be one or more subdirectories in the directory 704.

Each object in the directory can be a constructor object, an activator object, or both. A constructor object can be controlled to query the defibrillator for medical information whereas an activator object can be controlled to configure the defibrillator 402. Those objects that are to be exposed have predefined names (or "well-known" names in the idioms of software engineering) so that the software agent may use these well-known names to invoke the objects in the directory 704 via the device interface 502. These well-known names may be composed of any combination of letters, numbers, or symbols so long as each combination is unique to invoke an object in the directory 704.

When an object is exported from the directory 704 via the device interface 502, the object is imported into the software agent via the agent interface 512 as an element 716, which is structured in a language that contains the data of the object and that describes the data of the object. In other words, the exported object appears as an arrangement of data that is understood by the software agent, thereby allowing ease of data processing. The language to structure the data may use a number of textual tags to describe the data of the object. An example language includes Extensible Markup Language (XML), and in such a case, the element 716 is an XML element.

Upon receiving the element 716, the agent session manager 514 interacts with the set of agent rules 516 to invoke a presentation tool from a set of presentation tools 522. For example, the element 716 may invoke a presentation tool 702 so that a user interface may display the data of the element 716 on the personal digital assistant 404. A number of presentation tools may be used, such as stringed functions, pick values, pick lists, check lists, radio buttons, and pull down menus. Each presentation tool analyzes the element 716 for displaying by parsing out the attributes of the element 716, such as label, field, and parameter name. For example, the element 716 may represent a shock waveform that has four valid levels of energy; a presentation tool may represent the element 716 as four radio buttons with each radio button displaying a valid level of energy.

Figure 8:
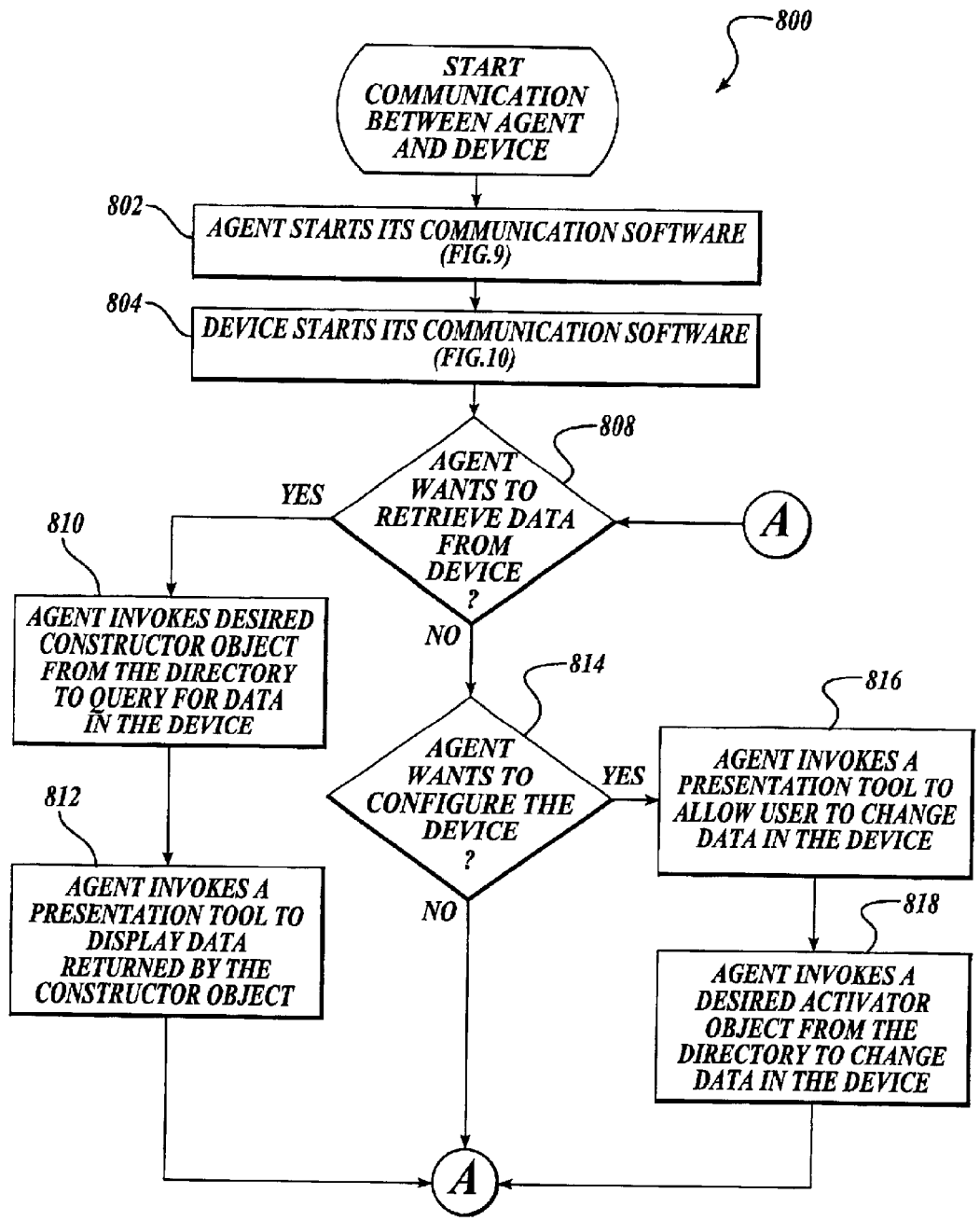
FIG. 8 is a process diagram illustrating a software flow to establish communication between a software agent and a medical device according to one embodiment of the invention.
Figure 9:
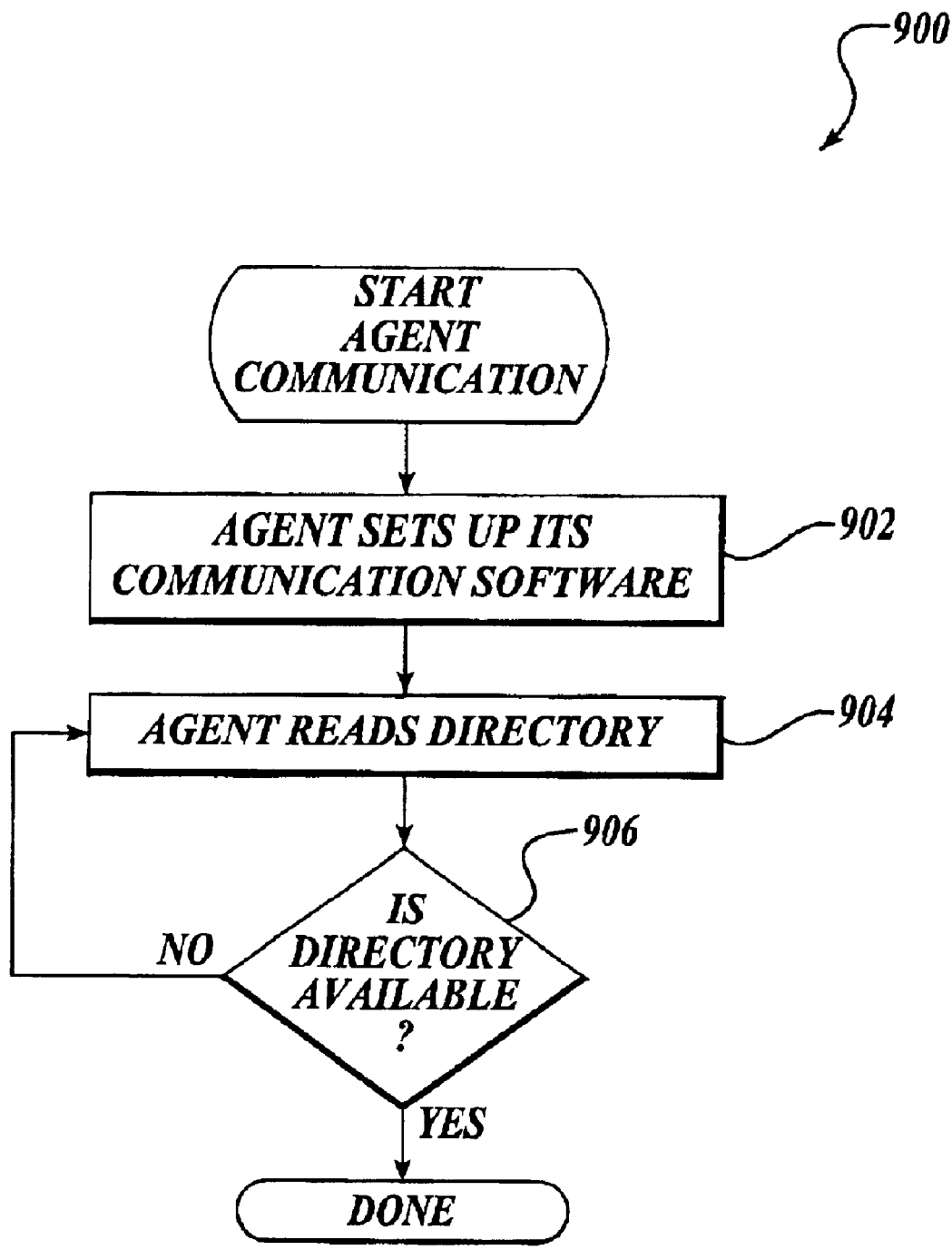
FIG. 9 is a process diagram illustrating a software flow to ready a software agent for communication according to one embodiment of the invention.
Figure 10:
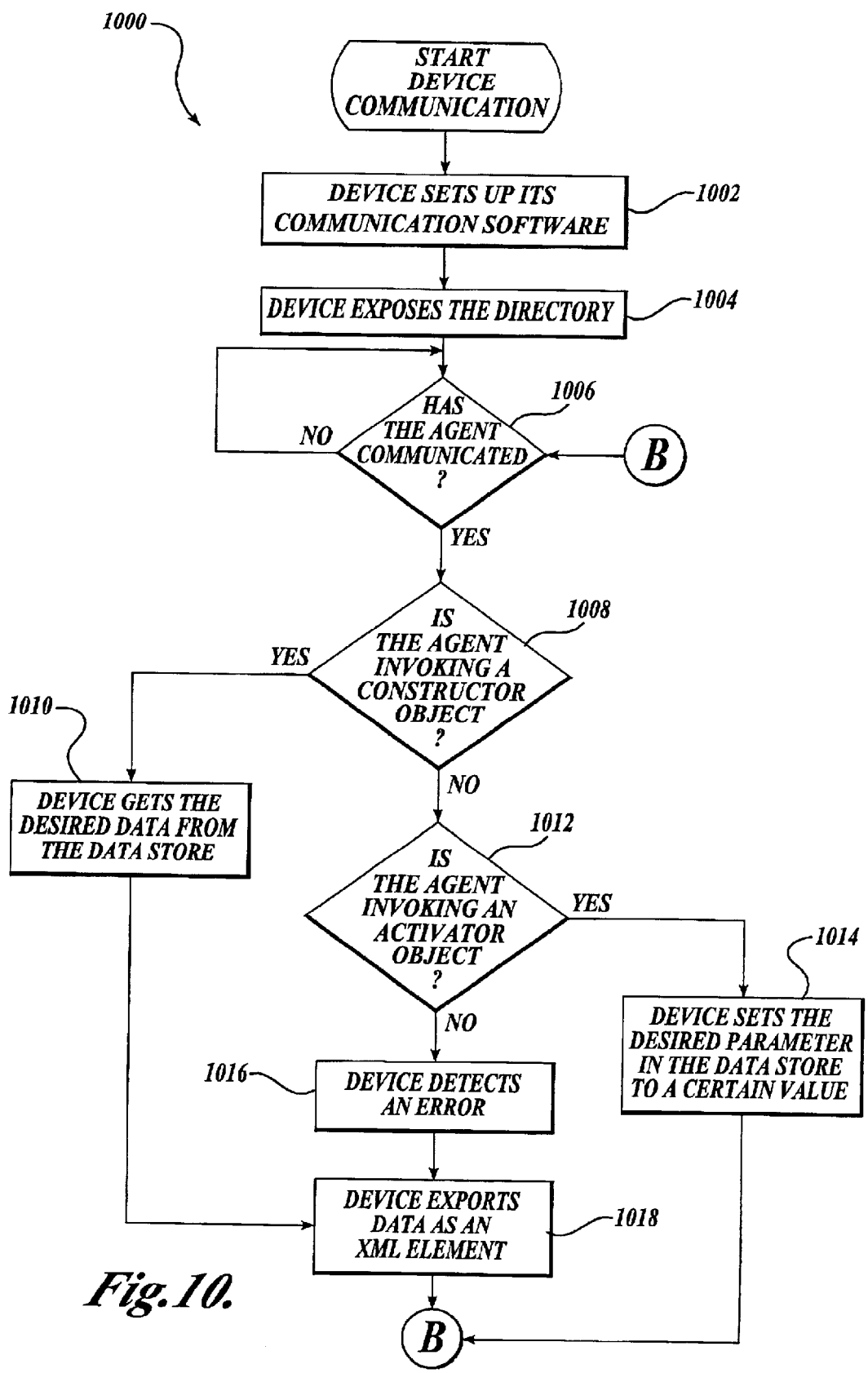
FIG. 10 is a process diagram illustrating a software flow to ready a medical device for communication according to one embodiment of the invention.

The communication between the defibrillator 402 and the software agent that resides on the personal digital assistant 404 can be further clarified by referring to a process 800 shown in FIG. 8. The communication begins when either the software agent starts the communications process as shown in a block 802 or the defibrillator 402 starts the communications process as shown in block 804. FIG. 9 illustrates in greater detail the process by which the software agent starts its communications software, and FIG. 10 illustrates in greater detail the process by which the defibrillator 402 starts its communications software.

Regardless of whether the software agent or the defibrillator initiates the communication, the process 800 proceeds to a decision block 808 where a determination is made as to whether the software agent wants to retrieve data from the defibrillator 402. If so, processing proceeds to a block 810 where a desired constructor object from the directory in the defibrillator 402 is invoked by the software agent to query and retrieve the desired medical information in the defibrillator 402. Next, at block 812, the software agent invokes a presentation tool to display the returned medical information in the form of an element, such as the element 716. When the processing at block 812 is finished, the process 800 enters node A and loops back to the decision block 808 again.

If the software agent does not want to retrieve the medical information from the defibrillator 402, the decision block 808 branches to a decision block 814, which determines whether the software agent wants to configure the defibrillator 402. If the answer to the decision block 814 is NO, the process 800 enters the node A and loops back to the decision block 808. If the answer at decision block 814 is YES, processing proceeds to block 816, where the software agent invokes a presentation tool to allow a user to change data. Next, at a block 818, the software agent invokes a desired activator object from a number of activator objects in the defibrillator 402 to change medical information in the defibrillator 402, and thereby configure the defibrillator 402. After the completion of processing in the block 818, processing proceeds to enter the node A, which leads back to the decision block 808 again.

As discussed above, for proper communication, the software agent may start its communications software as shown in FIG. 9. A process 900 begins by having the software agent set up its communication software at block 902. This may include selecting a desired set of communication protocols and setting up other communication parameters. Because the process of setting up a piece of communication software is considered to be well known, it need not be further discussed.

Once the software agent has successfully set up its communications software, the software agent attempts to read the directory of objects on the defibrillator 402 at a block 904 so as to verify that the software agent is communicatively coupled to the defibrillator 402. After attempting to read the directory, processing proceeds to a decision block 906 to determine whether the directory is available. If the software agent cannot read the directory, the software agent loops back to block 904 to attempt another try at reading the directory. Once the directory can be read by the software agent, processing returns to the block 804 in FIG. 8.

FIG. 10 shows a process 1000 that illustrates one method for starting the communications software of the defibrillator 402. Block 1002 is the beginning of the process 1000 where the defibrillator 402 sets up its communications software. The process of setting up includes selecting either wired or wireless communication protocols as well as setting up other communication parameters. The details of selecting and initiating a communications protocol are well known to those of ordinary skill in the art and therefore are not discussed in further detail.

After the communications software is set up, the defibrillator 402 exposes the directory of objects at block 1004. Each exposed object has a well-known name that the software agent can use to invoke the functionality of the exposed object. An exposed constructor object can be used to query the defibrillator 402 for medical information, and the exposed activator object can be used to change one or more parameters and thereby alter the operation of the defibrillator 402. If an exposed object is a constructor object as well as an activator object, then this exposed object can be used to query and configure the defibrillator 402.

Next, the process 1000 waits until the software agent communicates with the defibrillator 402 as represented by a decision block 1006. If the software agent has not communicated with the defibrillator, the answer to the decision block 1006 is NO, and the process 1000 loops back to the decision block 1006 again to wait until the software agent has communicated with the defibrillator. Once the answer to decision block 1006 is YES, the processing proceeds to a decision block 1008 where it is determined whether the software agent is invoking a constructor object. If the answer to the decision block 1008 is YES, the defibrillator 402 gets the desired medical information from the datastore. For example, if the desired medical information is patient data, the defibrillator 402 gets the patient data from the datastore 506. After the desired medical information is obtained, the defibrillator 402 exports the medical information to the software agent as an element, such as element 716, at a block 1018. Processing then proceeds from the block 1018 to enter a node B and loops back to the decision block 1006 again.

If the answer to the decision 1008 is NO, the process 1000 determines whether the software agent is invoking an activator object at a block 1012. If the software agent is indeed invoking an activator object, the program execution proceeds to a block 1014 where the defibrillator 402 sets a desired parameter in the datastore to a certain value. Afterwards, the process 1000 proceeds to enter the node B from the block 1014 and loops back to the decision block 1006 again.

The process 1000 enters a block 1016 if the answer to the decision block 1012 is NO. In this case, the defibrillator 402 has detected an error because it cannot understand the communication from the software agent. The defibrillator 402 will then export the error to the software agent as an element so that the software agent can further analyze the error.

The foregoing discussion uses the defibrillator 402 as an example of a medical device, but such a use is not meant to be limiting because the medical device can be any device that is capable of applying a therapy to a patient (a therapeutic device) or monitoring a patient parameter such as ECG, heart rate, blood pressure, etc. (a monitoring device). Also, the personal digital assistant 404 is used as an example of a computing device that may execute the software agent, but any computing device that can execute the software agent is within the scope of the present invention. Finally, although the process steps described above and shown in FIGS. 8–10 are shown in a particular sequence, it would be apparent to those skilled in the art that such steps could be performed in a different order and still achieve the functionality described.

While the preferred embodiment of the invention has been illustrated and described, it will be appreciated that various changes can be made therein without departing from the scope of the invention. It is therefore intended that the scope of the invention be determined from the following claims and equivalents thereto.

The embodiments of the invention in which an exclusive property or privilege is claimed are defined as follows:

1. A system for communicating medical information, comprising:
   a medical device installed with a version of software; and
   a software agent communicatively coupled to the medical device for interacting with the medical device, wherein the software agent interacts with the medical device irrespective of correspondence with the version of software installed on the medical device the software agent accessing a directory in the medical device to invoke one or more objects having well-known names in the directory and thereby access information in the medical device.

2. The system of claim 1, wherein the information includes medical information.

3. The system of claim 2, wherein the software agent interacts with the medical device by setting the medical information of the medical device.

4. The system of claim 2, wherein the software agent interacts with the medical device by retrieving the medical information from the medical device.

5. The system of claim 2, wherein the software agent interacts with the medical device by configuring the medical device.

6. The system of claim 1, further comprising another software agent communicatively coupled to the software agent.

7. The system of claim 1, further comprising a data management system communicatively coupled to the software agent.

8. The system of claim 1, wherein the information is structured in a language that contains the data and that describes the data wing a number of textual tags.

9. The system of claim 1, wherein the language includes Extensible Markup Language (XML), wherein data is structured as an XML element.

10. The system of claim 1, wherein each object is formed in a language that contains both configuration data and patient data and describes both the configuration data and the patient data using textual tags when the object is exported external to the medical device.

11. A system for communicating medical information, comprising:
   a medical device installed with a version of software;
   a software agent communicatively coupled to the medical device for interacting with the medical device, wherein the software agent interacts with the medical device irrespective of correspondence with the version of software installed on the medical device; and
   another medical device installed with another version of software, the software agent being communicatively coupled to the another medical device without regard to the another version of software installed on the another medical device, and wherein the another medical device retrieves from the software agent the medical information that the software agent retrieves from the medical device.

12. The system of claim 1, further comprising an output device communicatively coupled to the software agent.

13. The system of claim 12, wherein the output device is selected from a group consisting of a printer, a waveform display, a video recorder, a debugging machine, a data card, a cell phone, a therapeutic device trainer, a modem, an ECG monitor, a personal computer, an alarm system, a voice storage system, a personal digital assistant, a service test system, and a manufacturing test system.

14. The system of claim 13, wherein the output device is communicatively coupled to the software agent via a wired local area network.

15. The system of claim 13, wherein the output device is communicatively coupled to the software agent via a wireless local area network.

16. A system for communicating medical information, comprising:
   a therapeutic device for storing data and being installed with a version of software;
   a software agent to present a user interface to communicate with the therapeutic device; and
   an interface for communicatively coupling the therapeutic device to the software agent irrespective of correspondence of the software agent to the version of software of the therapeutic device, the software agent accessing a directory in the therapeutic device to invoke one or more objects having well-known names in the directory and thereby access data in the therapeutic device, and the interface having a therapeutic portion that exposes data from the therapeutic device and a software agent portion that obtains the data so that the user interface is invoked upon receiving the data.

17. The system of claim 16, wherein the software agent includes a set of presentation tools that invoke the user interface.

18. The system of claim 17, the directory including a number of constructor objects and a number of activator objects, each constructor object being controllable from the set of presentation tools to query the therapeutic device for the data, and each activator object being controllable from the set of presentation tools to configure the therapeutic device.

19. The system of claim 18, wherein each object in the directory has one of the well-known names so that the software agent may use the well-known name of the object to invoke the object in the directory.

20. The system of claim 16, wherein the data obtained by the agent portion of the interface is structured in a language that contains the data and that describes the data using a number of textual tags.

21. The system of claim 16, further comprising another therapeutic device communicatively coupled to the software agent, the another therapeutic device being reconfigurable by the software agent based on the data obtained from the therapeutic device by the software agent.

22. The system of claim 16, further comprising an output device communicatively coupled to the software agent.

23. The system of claim 22, wherein the output device is selected from a group consisting of a printer, a waveform display, a video recorder, a debugging machine, a data card, a cell phone, a therapeutic device trainer, a modem, an ECG monitor, a personal computer, an alarm system, a voice storage system, a personal digital assistant, a service test system, and a manufacturing test system.

24. The system of claim 23, wherein the output device is communicatively coupled to the software agent via a wired local area network.

25. The system of claim 23, wherein the output device is communicatively coupled to the software agent via a wireless local area network.

26. The system of claim 16, further comprising a data management system communicatively coupled to the software agent.

27. A system for remotely communicating with a medical device, comprising:
 a defibrillator for storing data and being installed with a version of software; and
 a personal digital assistant being operative to communicate with the defibrillator to access the data irrespective of the software version of the defibrillator, the software agent accessing a directory in the medical device to invoke one or more objects having well-known names in the directory and thereby access the data in the medical device.

28. The system of claim 27, wherein the personal digital assistant communicates with the defibrillator by setting data in the defibrillator.

29. The system of claim 27, wherein the personal digital assistant communicates with the defibrillator by retrieving data from the defibrillator.

30. The system of claim 27, wherein the personal digital assistant communicates with the defibrillator by configuring the data in the defibrillator.

31. The system of claim 27, wherein the defibrillator includes an interface that exposes the directory of objects, a number of objects referencing data relating to the configuration of the defibrillator, and a number of other objects referencing data relating to one or more patients treated by the defibrillator.

32. The system of claim 31, wherein each object in the directory is selected from a group consisting of an inbox, an outbox, device data, patient data, and a root directory.

33. The system of claim 31, wherein the personal digital assistant includes an interface allowing the receipt of the data structured in a language that contains the data and that describes the data through textual tags.

34. The system of claim 33, wherein the language includes Extensible Markup Language (XML), wherein data is structured as an XML element.

35. A system for remotely communicating with a medical device, comprising:
 a defibrillator for storing data and being installed with a version of software;
 a personal digital assistant being operative to communicate with the defibrillator to access the data irrespective of correspondence to the software version of the defibrillator; and
 another defibrillator installed with a software agent, the another defibrillator being communicatively coupled to the defibrillator via the software agent without regard to the version of software installed on the defibrillator, and wherein the another defibrillator retrieves from the defibrillator the medical information that is stored in the defibrillator.

36. A medical device, comprising:
 hardware to apply a therapy to a patient according to a set of therapeutic rules;
 one or more data storage devices for storing configuration data and patient data; and
 a common interface for exporting either the configuration data or the patient data, both the configuration data and the patient data being organized in one or more subdirectories of a directory.

37. The medical device of claim 36, wherein both the configuration data and the patient data are structured as objects in one or more subdirectories, wherein each object is formed in a language that contains both the configuration data and the patient data and that describes both the configuration data and the patient data using textual lags when the object is exported external to the medical device.

38. The medical device of claim 37, wherein a number of objects in one or more subdirectories are defined as constructors, wherein a number of other objects in one or more subdirectories are defined as activators, the constructor being invokable external to the medical device to query an object the activator being invokable external to the medical device to change an object.

39. The medical device of claim 36, further comprising a piece of communication software that contains wired communication protocols and another piece of communication software that contains wireless communication protocols, the device session manager selectively interacting with one of the two pieces of communication software to communicate external to the medical device.

40. The medical device of claim 39, further comprising a device session manager for coordinating the interaction among the number of therapeutic rules, the configuration data, patient data, and one of the two pieces of communication software.

41. The medical device of claim 39, wherein the wired communication protocols include File Transfer Protocol (FTP), Transmission Control Protocol (TCP), Internet Protocol (IP), Lightweight Directory Access Protocol (LDAP), Simple Object Access Protocol (SOAP), Common Object Request Broker Architecture (CORBA) protocol, RS-232-C protocol, HyperLAN, and IEEE 802.x protocols, and wherein the wireless communication protocols include Object Exchange (OBEX) protocol, Infrared Data Association (IrDA) protocols, and Bluetooth protocols.

42. A terminal for communicating with a medical device that stores data, the medical device being installed with a version of software, the terminal comprising:
 a data storage device for storing a set of presentation tools;
 a user interface being invokable by a presentation tool; and
 an interface for importing data stored in the medical device and for allowing the user interface to configure the medical device irrespective of correspondence to the version of software of the medical device, wherein the interface exposes a directory of objects on the medical device so that each object can be accessed, each object referencing data relating to the medical device, and wherein the data to configure the medical device is structured in a language that contains the data and that describes the data through textual tags.

43. The terminal of claim 42, wherein the language includes Extensible Markup Language (XML), wherein the data is structured as an XML element, and wherein upon receiving the data as an XML element, the set of presentation tools are invoked to present the user interface.

44. The terminal of claim 43, wherein the terminal includes a set of agent rules to determine which presentation tool is invoked when the XML element is received by the terminal.

45. The terminal of claim 44, further comprising a device session manager for coordinating the interaction among the set of presentation tools, the user interface, the interface, and the set of agent rules.

46. The terminal of claim 45, further comprising a piece of communication software that contains wired communication protocols and another piece of communication software that contains wireless communication protocols, the device session manager selectively interacting with one of the two pieces of communication software to communicate external to the terminal.

47. The terminal of claim 46, wherein the wired communication protocols include File Transfer Protocol (FTP), Transmission Control Protocol (TCP), Internet Protocol (IP), RS-232-C protocol, and IEEE 802.x protocol, and wherein the wireless communication protocols include Object Exchange (OBEX) protocol and Infrared Data Association (IrDA) protocols.

48. A method for communicating between a medical device and a terminal, comprising:
  establishing a communication session between the medical device and the terminal by selecting a wired communication protocol or a wireless communication protocol;
  exposing a directory of objects on the medical device so that each object can be accessed by the terminal, each object referencing data relating to the medical device; and
  presenting a user interface component to configure the medical device when data is imported into the terminal, the data being structured in a language that contains the data and that describes the data.

49. The method of claim 48, wherein the act of exposing a directory of objects includes exposing objects that have well-known names so that each object can be accessed by the terminal using the well-known name of the object.

50. The method of claim 49, wherein the directory of objects includes activator objects, each activator object being controllable by the user interface component to configure the medical device.

51. The method of claim 49, wherein the directory of objects includes constructor objects, each constructor object being controllable by the user interface component to query the medical device for a piece of data.

52. The method of claim 48, wherein the method does not proceed in the order presented.

53. A medical device comprising:
  hardware to apply a therapy to a patient according to a set of therapeutic rules;
  one or more data storage devices for storing configuration data and patient data; and
  a processor for exposing a directory of objects having well-known names that may be used to invoke the objects external to the medical device, a set of objects being invokable to retrieve configuration data or the patient data, and another set of objects being invokable to change the configuration data so that the therapy to be applied to the patient is changed.

54. The medical device of claim 53, wherein each well-known name includes one or more letters.

55. The medical device of claim 53, wherein each well-known name includes one or more numbers.

56. The medical device of claim 53, wherein each well-known name includes one or more symbols.

57. The medical device of claim 53, wherein each well-known name is composed from a combination of letters, numbers, and symbols.

58. A system comprising:
  a defibrillator having a memory storing objects relating to patient data and defibrillator configuration data; and
  a device to communicate with the defibrillator to access the patient data and the defibrillator configuration data via the objects,
  wherein the data is structured in a language that contains the data and describes the data through textual tags.

59. The system of claim 58, wherein the language includes Extensible Mark Language (XML), the data being structured as one or more XML elements.

60. The system of claim 58, further comprising a second defibrillator having a memory storing objects relating to patient data and defibrillator configuration data, wherein the device communicates with the second defibrillator to access the patient data and the defibrillator configuration data via the objects stored by the memory in the second defibrillator.

* * * * *

UNITED STATES PATENT AND TRADEMARK OFFICE
CERTIFICATE OF CORRECTION

PATENT NO. : 6,957,102 B2  Page 1 of 1
APPLICATION NO. : 10/016507
DATED : October 18, 2005
INVENTOR(S) : H. Ward Silver et al.

It is certified that error appears in the above-identified patent and that said Letters Patent is hereby corrected as shown below:

In column 9, line 30, in claim 1, delete "device" and insert -- device, --, therefor.

In column 9, line 54, in claim 8, delete "wing" and insert -- using --, therefor.

In column 12, line 15, in claim 37, delete "lags" and insert -- tags --, therefor.

In column 12, line 22, in claim 37, delete "object" and insert -- object, --, therefor.

In column 13, line 19, in claim 47, delete "protocol," and insert -- protocols, --, therefor.

In column 14, line 5, in claim 53, delete "device" and insert -- device, --, therefor.

In column 14, line 37, in claim 59, delete "Mark" and insert -- Markup --, therefor.

Signed and Sealed this

Thirty-first Day of August, 2010

David J. Kappos
*Director of the United States Patent and Trademark Office*